United States Patent [19]

Grusmark

[11] Patent Number: 4,991,755

[45] Date of Patent: * Feb. 12, 1991

[54] TOOTHPASTE DISPENSER WITH TIMER ASSEMBLY

[76] Inventor: Stephen Grusmark, 2901 S. Bayshore Dr., #15C, Coconut Grove, Fla. 33133

[*] Notice: The portion of the term of this patent subsequent to Jun. 6, 2006 has been disclaimed.

[21] Appl. No.: 361,061

[22] Filed: Jun. 5, 1989

Related U.S. Application Data

[63] Continuation-in-part of Ser. No. 115,803, Nov. 2, 1987, Pat. No. 4,836,415.

[51] Int. Cl.⁵ .................................................. B67D 5/08
[52] U.S. Cl. ...................................... 222/638; 222/39; 222/192; 206/216; 368/10
[58] Field of Search .......................... 368/1, 10, 98–100, 368/93; 222/638, 192, 106, 39; 116/307; 132/308, 309; 206/216; 221/2, 15

[56] References Cited

U.S. PATENT DOCUMENTS

| | | |
|---|---|---|
| 628,472 | 7/1899 | Keim . |
| 1,080,464 | 12/1913 | Larsen . |
| 1,923,978 | 8/1933 | Hill .................... 368/93 X |
| 1,973,390 | 9/1934 | Plants .................... 368/93 |
| 2,209,691 | 7/1940 | Fraser .................... 368/98 X |
| 2,706,378 | 4/1955 | Goldman .................... 368/98 |
| 2,824,418 | 2/1958 | Hilbert .................... 368/93 |
| 2,926,487 | 3/1960 | Stone .................... 368/1 |
| 3,021,666 | 2/1962 | Stone .................... 368/1 |
| 3,129,845 | 4/1964 | Musser . |
| 3,542,519 | 11/1970 | Montalto et al. . |
| 3,783,364 | 1/1974 | Gallanis et al. . |
| 3,827,232 | 8/1974 | Bassett .................... 368/100 |
| 4,010,869 | 3/1977 | Adamo . |
| 4,035,793 | 7/1977 | Jennings .................... 368/98 X |
| 4,311,448 | 1/1982 | Strauss .................... 368/10 X |
| 4,367,955 | 1/1983 | Ballew . |
| 4,382,688 | 5/1983 | Machamer . |
| 4,448,541 | 5/1984 | Wirtschafter . |
| 4,673,106 | 6/1987 | Fishmann .................... 222/192 X |
| 4,776,492 | 10/1988 | Gallo .................... 222/192 X |
| 4,827,951 | 5/1989 | Grussmark .................... 222/192 X |
| 4,836,415 | 6/1989 | Grussmark .................... 222/192 X |

FOREIGN PATENT DOCUMENTS 1551946 9/1979 United Kingdom ................ 368/100

Primary Examiner—Andres Kashnikow
Assistant Examiner—Gregory L. Huson
Attorney, Agent, or Firm—Lloyd L. Zickert

[57] ABSTRACT

A toothpaste dispenser including a timer device structured so that a person will receive a signal to indicate a time period of sufficient length has elapsed for the brushing of teeth. The timer assembly may include an activating structure directly thereon such as on an exposed face thereof wherein the activating structure is readily accessible from an extension of the dispenser. In another embodiment, the activating structure associated with the timer assembly is mounted at least partially on the interior of the housing of the toothpaste dispenser and connected to a dispensing plunger such that the time period for brushing teeth is automatically set concurrently to depressing of the plunger for the dispensing of toothpaste from the container.

9 Claims, 1 Drawing Sheet

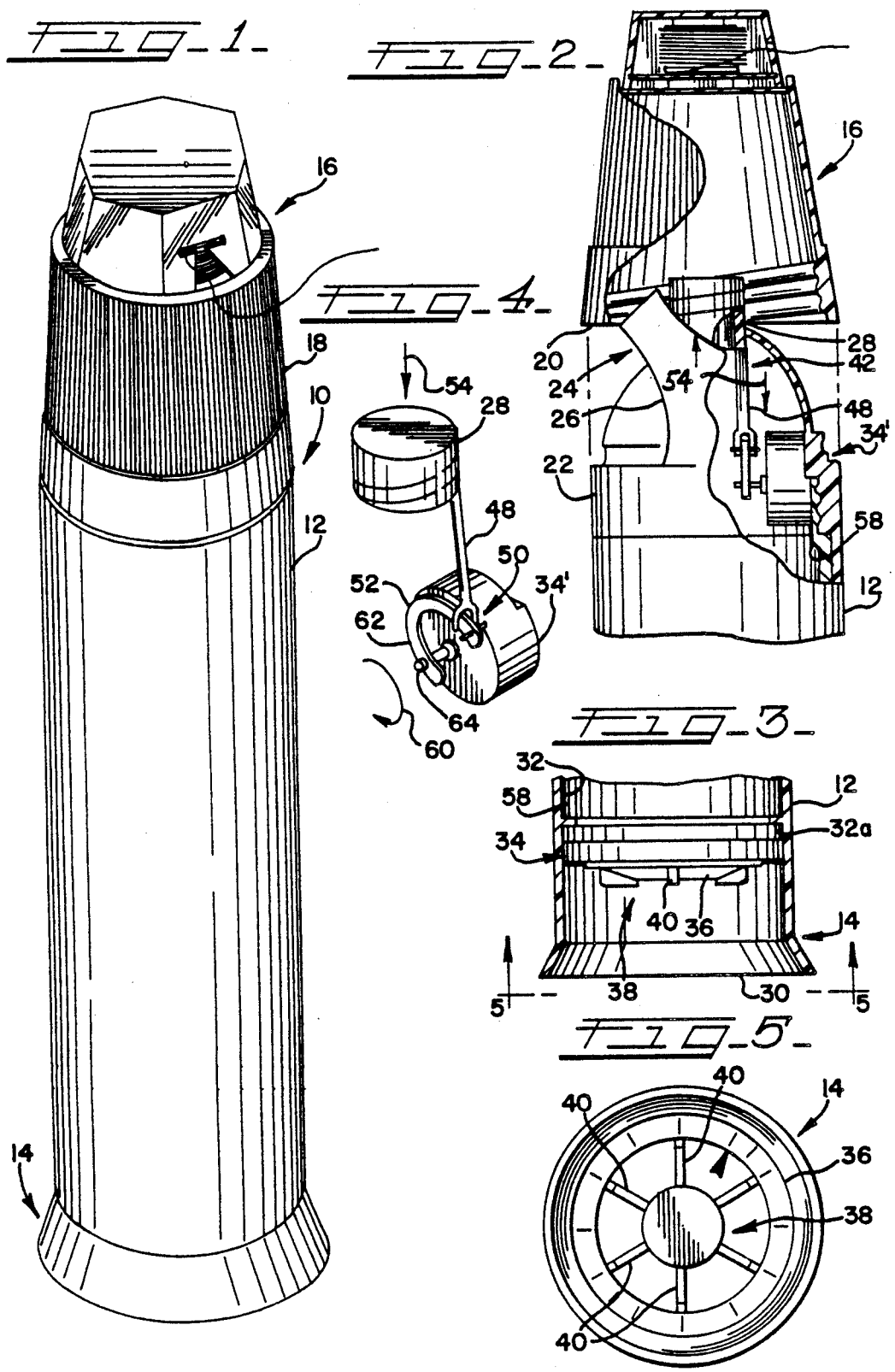

TOOTHPASTE DISPENSER WITH TIMER ASSEMBLY

This is a continuation-in-part-application of presently pending U.S. patent application Ser. No. 115,803 filed on Nov. 2, 1987, now U.S. Pat. No. 4,836,415.

BACKGROUND OF THE INVENTION

1. Field of the Invention

This invention relates to a dispenser for toothpaste including a housing having a container disposed on the interior thereof and further wherein the dispenser is used in combination with a timer assembly for indicating to the user when sufficient time has elapsed for the brushing of teeth.

2. Description of the Prior Art

Representative prior art is found in U.S. letters patent 1,080,464 which is directed to a poison bottle having an indicator such as a belt, attached thereto and thereby defining a signal means. The U.S. letters patents 628,472 is directed to a mechanical time alarm for use in combination with a telephone.

A dispenser for retaining toothbrush and floss is disclosed in Fishman U.S. Pat. No. 3,673,106. A mechanical timer apparatus is disclosed in the Wirtschafter U.S. Pat. No. 4,448,541. Similarly, a dental rack and timer associated therewith is disclosed in the Hill U.S. Pat. No. 1,923,978.

A dispenser and timing device in disclosed in Musser U.S. Pat. No. 3,129,845. An animated timing device is disclosed in the Hilbert U.S. Pat. No. 2,824,418. Plants U.S. Pat. No. 1,973,390 also discloses a timing device for brushing operation wherein the device is mounted on a rack or holder for a toothbrush.

Additional timing devices disclosed for a variety of different types of dispensers are shown in the following U.S. patents. Gallanis U.S. Pat. No. 3,783,364 discloses an electrical appliance having a clock-like structure and Montalto et al U.S. Pat. No. 3,542,519 discloses a toothbrush timer usage indicator.

Ballew U.S. Pat. No. 4,367,955; U.S. Pat. No. Adamo U.S. Pat. No. 4,010,869 and Machamer U.S. Pat. No. 4,382,688 all disclose various dispensing devices having a timer associated therewith to indicate elapsed time or time for dispensing.

SUMMARY OF THE INVENTION

The present invention relates to a dispensing assembly for toothpaste or like material and more particularly to a dispenser assembly having a timer mechanism associated therewith.

In one preferred embodiment of the present invention, the timer assembly is mounted at least partially on the interior of a base. The base is secured to the lower end of the housing and is structured and disposed for supporting the housing as well as the toothpaste container on the interior thereof on any type of conventional supporting surface. The base includes an open face and/or a hollow interior configuration for placement of the timer therein. The timer includes an actuating assembly preferably mounted on the exposed face of the timer. The actuator assembly is therefore readily accessible for manual manipulation and activation of the timer assembly. The opposite end of the housing may include an activating plunger which is associated with a valve mechanism or like structure for the automatic dispensing of the toothpaste from the interior of the container maintained within the housing. Depending upon the particular structure utilized, the toothpaste container may in fact be a part of the housing but is, as set forth above, located on the interior of the housing. The plunger therefore, when depressed, serves to dispense a predetermined amount of toothpaste preferably onto a toothbrush for brushing ones teeth.

In another preferred embodiment of the present invention, the timer assembly is mounted on the interior of the housing generally adjacent to and in connection with the dispensing plunger. In such an embodiment, the plunger is normally maintained in a non-dispensing position and an associating activating means is connected thereto normally positioned in a non-actuating position.

Relative structure and interconnection between the dispensing plunger and the activating means is such as to allow for automatic, concurrent dispensing of the toothpaste upon depression of the plunger into a dispensing position. Such force being exerted on the dispensing plunger will cause the actuating means to actuate the timer assembly causing a predetermined amount of elapsed time to begin running. When such time has elapsed, the timer assembly, regardless of the embodiment utilized, may include an audible signal to indicate to the user when sufficient time has elapsed for brushing ones teeth. Also, the timer assembly may be structured such that one may effectively hear the "workings" of the timer assembly and when such sound stops, the one brushing his or her teeth is aware that sufficient time has elapsed for brushing.

Other features associated with the assembly of the present invention may include an automatic floss dispenser mounted on an external cap or closure structure attached to the upper or free end of the housing in substantially covering and protecting relation to the dispensing plunger and the activating means when the latter embodiment is utilized.

BRIEF DESCRIPTION OF THE DRAWINGS

For a fuller understanding of the nature of the present invention, reference should be had to the following detailed description taken in connection with the accompanying drawings in which:

FIG. 1 is a perspective view of a dispensing housing and container of the present invention.

FIG. 2 is a sectional view along in partial exploded and cut-away format showing the interior structure of one embodiment of the present invention.

FIG. 3 is a fragmentary sectional view showing details of the timer structure associated with another embodiment of the present invention.

FIG. 4 is a perspective view in detail showing components of the dispensing plunger and activating means associated with the timer and dispenser of the contents of the housing of the embodiment of FIG. 2.

FIG. 5 is bottom plan view in the embodiment of FIG. 3 taken along line 5—5 thereof.

Like reference numerals refer to like parts throughout the several views of the drawings.

DETAILED DESCRIPTION OF THE PREFERRED EMBODIMENT

As shown in FIG. 1, the present invention is directed to a container and dispensing assembly for dispensing toothpaste, automatically from a toothpaste container. Such devices are commercially available and known in the market as "pumps". The subject invention however, is directed to a timer structure used in combination with a dispensing means and/or assembly generally indicated as 10. The dispenser 10 may be more specifically defined as including an elongated housing 12 having a support base portion generally indicated as 14 and a protective cover or cap generally indicated as 16 mounted on the opposite end of the housing 12 relative to the support base 14. The cover or cap 16 includes a surrounding, substantially hollow portion 18 having an open end as at 20 to fit on a peripheral outer surface portion 22 as best shown in FIG. 2. The closure 16 is obviously removable from its protective position relative to a dispensing mechanism 9 generally indicated as 24. The dispensing mechanism, includes a dispensing valve mechanism (only partially shown in detail of FIG. 2) including a flexible spout as at 26 and a dispensing plunger 28 which is normally biased or positioned in an upright non-dispensing position as shown in FIG. 2.

Further with regard to the embodiment of FIG. 1, the base 14 has an open face or ended structure as at 30 and a substantially hollow interior configuration at least along a portion thereof as at 32. An important feature of the present invention is the existence of a timer assembly generally indicated as 34 and including a timer mechanism 36 having an activating means generally indicated as 38 mounted on an exposed face thereof. As seen in FIG. 3, the container 58 is supported in the interior 32 of the housing 12 just above the timer 34 on an annular shoulder 32a. A plurality of outwardly extending spaced apart wing or flange members 40 protrude from the face and are defined as part of the activating means 38. These flanges or wings 40 are dimensioned and disposed for at least partial gripping of the fingers of the user. Suffice it to say that the placement of the timer assembly 34 on the interior 32 of the base 14 is such as to allow the flange members 40 to be readily accessible for gripping and rotation of the activating means 38. When such happens, the timer is activated once the activating means 38 is rotated to a predetermined position. Such position may be preset so as to allow a predetermined elapsed time to pass which the user, when brushing, may assume is sufficient to adequately clean the teeth. The actual workings of the timer assembly 34 are not shown for purposes of clarity but may be constructed similar to a wide variety of conventional timer mechanisms. A sound may serve as a signal wherein operation of the timer assembly 34 may occur continuously while giving off such sound and when such sound stops the brusher is made aware that sufficient time has passed to properly clean his teeth. Alternately, an audible sound may be associated with the timer assembly 34 for purposes of indicating to the brusher when sufficient time has elapsed.

In the embodiment of FIG. 2, the timer assembly is generally indicated as 34' and is mounted at least partially on the interior of the housing 12 in a position which is substantially adjacent to the dispensing plunger 28. Further, the actuating means is indicated as 42 and includes an elongated stem or connecting shaft 48 movably connected by a pivotal connection as at 50 to an activating member 52 on the face of the timer mechanism or a portion thereof 34' as shown in FIG. 4. Depression of the dispensing plunger 28 in accordance with directional arrow 54 serves to position the spout or nozzle 26 into a dispensing position thereby forcing the contents or toothpaste within the container as at 58 or interior of the housing 12 directly through the spout 26 to the toothbrush of the user. Concurrently, due to the interconnection of the stem or shaft 48, the depression of the plunger 28 in accordance with directional arrow 54 causes a rotation of the face of the timer due to the rotatable or pivotal connection 50 in accordance with directional arrow 60.

This rotation serves to activate the timer 34' marking when the time period begins to elapse which has been predetermined to adequately brush the teeth of the user.

Specific features of the activating means is shown in FIG. 4 includes an arcuate link 62 pivotally connected as at 64 causing a rotation of the mechanism and an activation of the timer assembly 34'.

Now that the invention has been described, what is claimed is:

1. A timer assembly used in combination with a toothpaste dispenser of the type including an elongated housing means having a base portion for supporting a toothpaste container therein and comprising:
   a. a plunger means movably mounted on said housing and disposed and structured to cause the dispensing of toothpaste from said container.
   b. said base comprising an open ended construction and a hollow interior portion communicating exteriorly of said housing through said open end,
   c. said timer assembly including an activating means disposed on an accessible portion of the timer and structured to selectively activate said timer,
   d. said timer assembly dimensioned and configured to be receivably secured within said hollow interior of said base and be supported by said housing, and
   e. said activating means disposed in an accessible position through said open end when said timer assembly is secured within said base.

2. An assembly as in claim 1 wherein said timer assembly is disposed in spaced relation to said plunger mean and is operable independently thereof.

3. An assembly as in claim 1 wherein said base and said timer assembly include congruent configurations, said activating means movably mounted on an exposed face of said timer assembly and said activating means and said exposed face being positioned in readily accessible position within said base through said open end.

4. An assembly as in claim 3 wherein said timer assembly includes a peripheral portion correspondingly configured to an inner periphery of said open end and mounted in confronting, supported engagement therein.

5. An assembly as in claim 4 wherein said timer assembly is removably mounted within said base.

6. A timer assembly used in combination with a toothpaste dispenser of the type including an elongated housing means having a base portion for supporting a toothpaste container therein and comprising:
   a. a plunger means movably mounted on said housing and disposed and structured to cause the dispensing of toothpaste from said container.
   b. said timer assembly including an activating means disposed on an accessible portion of the timer assembly and structured to selectively activate said timer,
   c. said housing including a hollow interior portion correspondingly dimensioned and configured to receive said timer assembly therein,
   e. said plunger means including a connecting assembly disposed to interconnect said plunger assembly to said activating means,
   f. said connecting assembly structured and disposed in driving relation to said activating means upon forced travel of said plunger means into a dispensing position, and g. whereby said timer assembly is activatable concurrently with dispensing of toothpaste from the toothpaste container.

7. An assembly as in claim 6 wherein said plunger assembly is normally biased in an outwardly, non-dispensing position and disposable against a biasing force into said dispensing position.

8. An assembly as in claim 7 wherein said connecting assembly comprises a connecting link secured to both said plunger assembly and said activating means of said timer assembly, said connecting link disposed and structured to drivingly position said activating means in an activating position concurrently when said plunger is positioned from said non-dispensing position to said dispensing position.

9. An assembly as in claim 8 wherein said activating means is biased into a non-activating position, both said plunger means and said activating means automatically returnable into a non-dispensing and non-activating position respectively upon release of positioning force from said plunger assembly.

* * * * *

UNITED STATES PATENT AND TRADEMARK OFFICE
CERTIFICATE OF CORRECTION

PATENT NO. : 4,991,755
DATED : February 12, 1991
INVENTOR(S) : Stephen M. Grussmark It is certified that error appears in the above-identified patent and that said Letters Patent is hereby corrected as shown below: ON TITLE PAGE:

Item [19] and [76] Inventor: should be --Stephen M. Grussmark--;
Col. 1, line 25, change "3,673,106" to --4,673,106--;
       line 30, after "device" change "in" to --is--;
       line 42, delete the second occurrence of "U.S. Pat. No.";
Col. 2, line 7, change "ones" to --one's--;
       line 27, change "ones" to --one's--;
       line 57, change "in" to --of--;
                change "of" to --in--;
Col. 3, line 13, delete the numeral "9";
Col. 4, line 9, delete "is";
       line 37, change "mean" to --means--;
       line 64, change "e." to --d.--;
       line 67, change "f." to --e.--; and
Col. 5, line 3, change "g." to --f.--.

Signed and Sealed this

Seventh Day of July, 1992

Attest:

DOUGLAS B. COMER

Attesting Officer      Acting Commissioner of Patents and Trademarks